(12) United States Patent
Ferek-Petric

(10) Patent No.: US 7,620,446 B2
(45) Date of Patent: Nov. 17, 2009

(54) MONITORING P-WAVES TO DETECT DEGRADATION OF ATRIAL MYOCARDIUM

(75) Inventor: Bozidar Ferek-Petric, Zagreb (HR)

(73) Assignee: Medtronic, Inc., Minneapolis, MN (US)

( * ) Notice: Subject to any disclaimer, the term of this patent is extended or adjusted under 35 U.S.C. 154(b) by 944 days.

(21) Appl. No.: 10/631,614

(22) Filed: Jul. 31, 2003

(65) Prior Publication Data

US 2005/0027321 A1 Feb. 3, 2005

(51) Int. Cl.
  *A61B 5/04* (2006.01)
(52) U.S. Cl. .................................................. 600/509
(58) Field of Classification Search ............ 607/27–29; 600/509–510
  See application file for complete search history.

(56) References Cited

U.S. PATENT DOCUMENTS

| | | | |
|---|---|---|---|
| 5,374,282 A | 12/1994 | Nichols et al. | |
| 5,458,621 A | 10/1995 | White et al. | |
| 5,792,192 A * | 8/1998 | Lu | 607/14 |
| 5,800,466 A | 9/1998 | Routh et al. | |
| 5,817,133 A * | 10/1998 | Houben | 607/9 |
| 5,824,021 A | 10/1998 | Rise | |
| 6,029,087 A | 2/2000 | Wohlgemuth | |
| 6,047,806 A * | 4/2000 | Sasse | 192/113.36 |
| 6,058,328 A * | 5/2000 | Levine et al. | 607/14 |
| 6,122,553 A | 9/2000 | Ideker et al. | |
| 6,205,357 B1 | 3/2001 | Ideker et al. | |
| 6,234,603 B1 | 5/2001 | Altfather et al. | |
| 6,514,195 B1 | 2/2003 | Ferek-Petric | |
| 6,604,000 B2 * | 8/2003 | Lu | 607/17 |

(Continued)

FOREIGN PATENT DOCUMENTS

EP 1 062 987 A2 12/2000

OTHER PUBLICATIONS

P. E. Dilaveris, G. K. Andrikopoulos, G. Metaxas, D. J. Richter, C. K. Avgeropoulou, A. M. Androulakis, E. J. Gialafos, A. P. Michaelides, P. K. Toutouzas, J. E. Gialafos (1999) Effects of Ischemia on P Wave Dispersion and Maximum P Wave Duration During Spontaneous Anginal Episodes; Pacing and Clinical Electrophysiology 22 (11), 1640-1647.*

(Continued)

*Primary Examiner*—George Manuel
*Assistant Examiner*—Christopher A Flory
(74) *Attorney, Agent, or Firm*—Michael C. Soldner

(57) ABSTRACT

An implantable medical device (IMD) monitors at least one characteristic of P-waves within an electrogram signal. By monitoring changes in the characteristic over time, the IMD detects degradation of the atrial myocardium. In some embodiments, the IMD detects ischemia, an increased probability of the occurrence of angina, or a risk of future atrial fibrillation based on changes in the characteristic over time. The IMD can include a memory to store information relating to the detection and other diagnostic information for retrieval and evaluation by a clinician, and/or an alarm to alert the patient of the detection. In some embodiments, the IMD switches out of an atrial-tracking ventricular pacing mode, decreases the maximum tracking rate for an atrial-tracking ventricular pacing mode, increases the aggressiveness of rate-responsive atrial pacing, and/or initiates or modifies delivery of a therapy, such as a drug or neurostimulation, in response to the identification.

32 Claims, 13 Drawing Sheets

U.S. PATENT DOCUMENTS

| | | | |
|---|---|---|---|
| 6,738,655 B1* | 5/2004 | Sen et al. | 600/374 |
| 6,741,890 B1* | 5/2004 | Seim et al. | 607/9 |
| 7,027,861 B2* | 4/2006 | Thompson | 607/4 |
| 7,107,093 B2* | 9/2006 | Burnes | 600/509 |
| 7,123,954 B2* | 10/2006 | Narayan et al. | 600/518 |
| 7,142,907 B2* | 11/2006 | Xue et al. | 600/509 |
| 2003/0036773 A1* | 2/2003 | Whitehurst et al. | 607/3 |
| 2003/0083587 A1 | 5/2003 | Ferek-Petric | 600/512 |
| 2004/0162590 A1* | 8/2004 | Whitehurst et al. | 607/17 |
| 2004/0215238 A1* | 10/2004 | van Dam et al. | 607/4 |
| 2007/0021679 A1* | 1/2007 | Narayan et al. | 600/518 |

OTHER PUBLICATIONS

Palma, Eugen C., et al., "Effect of Varying Atrial Sensitivity, AV Interval, and Detection Algorithm on Automatic Mode Switching", *Pace*, vol. 19, Nov. 1996, Part II, pp. 1734-1739.

Bonnet, et al., "Mode Switch Despite Undersensing of Atrial Fibrillation in DDD Pacing", *Pace*, vol. 19, Nov. 1996, Part II, pp. 1724-1728.

Ricci, et al., "Reliability of a New Algorithm for Automatic Mode Switching from DDDR to DDIR Pacing Mode in Sinus Node Disease Patients with Chronotropic Incompetence and Recurrent Paroxysmal Atrial Fibrillation", *Pace*, vol. 19, Nov. 1996, Part II, pp. 1719-1723.

Lam, et al., "Improved Efficacy of Mode Switching During Atrial Fibrillation Using Automatic Atrial Sensitivity Adjustment", *Pace*, vol. 22, Jan. 1999, Part I, pp. 17-25.

De Sisti, A. et al., "P Wave Duration and Morphology Predict Atrial Fibrillation Recurrence in Patients with Sinus Node Dysfunction and Atrial-Based Pacemaker," *Pace*, vol. 25, No. 11, p. 1546-1554 (Nov. 2002).

Dilaveris, P.E. et al., "Future Concepts in P Wave Morphological Analyses," *CEPR*, vol. 6, No. 3, p. 221-224 (2002).

Guo, X.H. et al., "Prognostic Significance of Serial P Wave Signal-Averaged Electrocardiograms Following External Electrical Cardioversion for Persistent Atrial Fibrillation," *Pace*, vol. 25, Part II, p. 299-304 (Jan. 2003).

* cited by examiner

MONITORING P-WAVES TO DETECT DEGRADATION OF ATRIAL MYOCARDIUM

TECHNICAL FIELD

The present invention relates to cardiac monitoring and, more particularly, to implantable medical devices that monitor electrical activity of the heart.

BACKGROUND

Ischemic heart disease and mitral valve disease are examples of conditions that cause the atrial myocardium to degrade. Ischemic heart disease leads to infarcted tissue within the atrial myocardium, and mitral valve disease leads to dilation and weakening of the atrial myocardium. Degradation of the atrial myocardium through these and other disease mechanisms can lead to patient discomfort and reduction in cardiac performance.

For example, both ischemic heart disease and atrial dilation may result in the onset of paroxysmal atrial fibrillation. The disorganized contractions of the atria during an episode of fibrillation are insufficient for proper ventricular filling, and atrial fibrillation can consequently lead to patient symptoms such as dizziness and shortness of breath. Atrial fibrillation is also conducive to the formation of potentially life-threatening emboli. Further, ischemic heart disease of the ventricles can lead to angina pectoris, which may occur spontaneously, or during periods of exercise or strong emotions.

SUMMARY

In general, the invention is directed to an implantable medical device (IMD) that monitors at least one characteristic of P-waves within an electrogram signal. By monitoring changes in the characteristic over time, the IMD detects degradation of the atrial myocardium. In some embodiments, the IMD detects ischemia, identifies a potential for the occurrence of angina, or identifies a risk of future atrial fibrillation prior to an occurrence of atrial fibrillation based on changes in the characteristic over time.

In exemplary embodiments, the IMD measures amplitudes and/or widths of P-waves within the signal. In some embodiments, the IMD calculates average P-wave amplitudes, P-wave width variabilities, and/or P-wave width dispersions for periods of time, and compares the calculated value for a current period of time to the calculated value for a previous period of time to detect degradation of the atrial myocardium.

In some embodiments, the IMD includes a memory to store information relating to the detection, and other diagnostic information for retrieval and evaluation by a clinician. Additionally, the IMD may include an alarm to alert the patient of the detection. In some embodiments, the IMD switches out of an atrial-tracking ventricular pacing mode, decreases the maximum tracking rate for an atrial-tracking ventricular pacing mode, increases the aggressiveness of rate-responsive atrial pacing, and/or initiates or modifies delivery of a therapy, such as a drug or neurostimulation, in response to the identification.

In one embodiment, the invention is directed to a method in which a signal that represents electrical activity within a heart of a patient is received via electrodes implanted within the patient. The signal is processed to monitor a characteristic of P-waves within the signal. Degradation of an atrial myocardium of the heart is detected based on the characteristic.

In another embodiment, the invention is directed to an implantable medical device comprising electrodes and a processor. The electrodes are implantable within a patient to detect a signal that represents electrical activity within a heart of the patient. The processor monitors a characteristic of P-waves within the signal, and detects degradation of an atrial myocardium of the heart based on the characteristic.

In another embodiment, the invention is directed to a computer-readable medium containing instructions. The instructions cause a programmable processor to monitor a characteristic of P-waves within a signal that represents electrical activity within a heart of a patient, and detect degradation of an atrial myocardium based on the characteristic.

In another embodiment, the invention is directed to a system comprising a therapy delivery device to deliver a therapy to a patient, and a monitoring device. The monitoring device monitors a characteristic of P-waves within a signal that represents electrical activity within a heart of the patient, detects degradation of an atrial myocardium of the heart based on the characteristic, and controls delivery of therapy by the therapy delivery device based on the detection.

In another embodiment, the invention is directed to a method in which a signal that represents electrical activity within a heart of a patient is received via electrodes implanted within the patient. The signal is processed to monitor a characteristic of P-waves within the signal, and a risk of atrial fibrillation is identified prior to occurrence of atrial fibrillation based on the characteristic.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
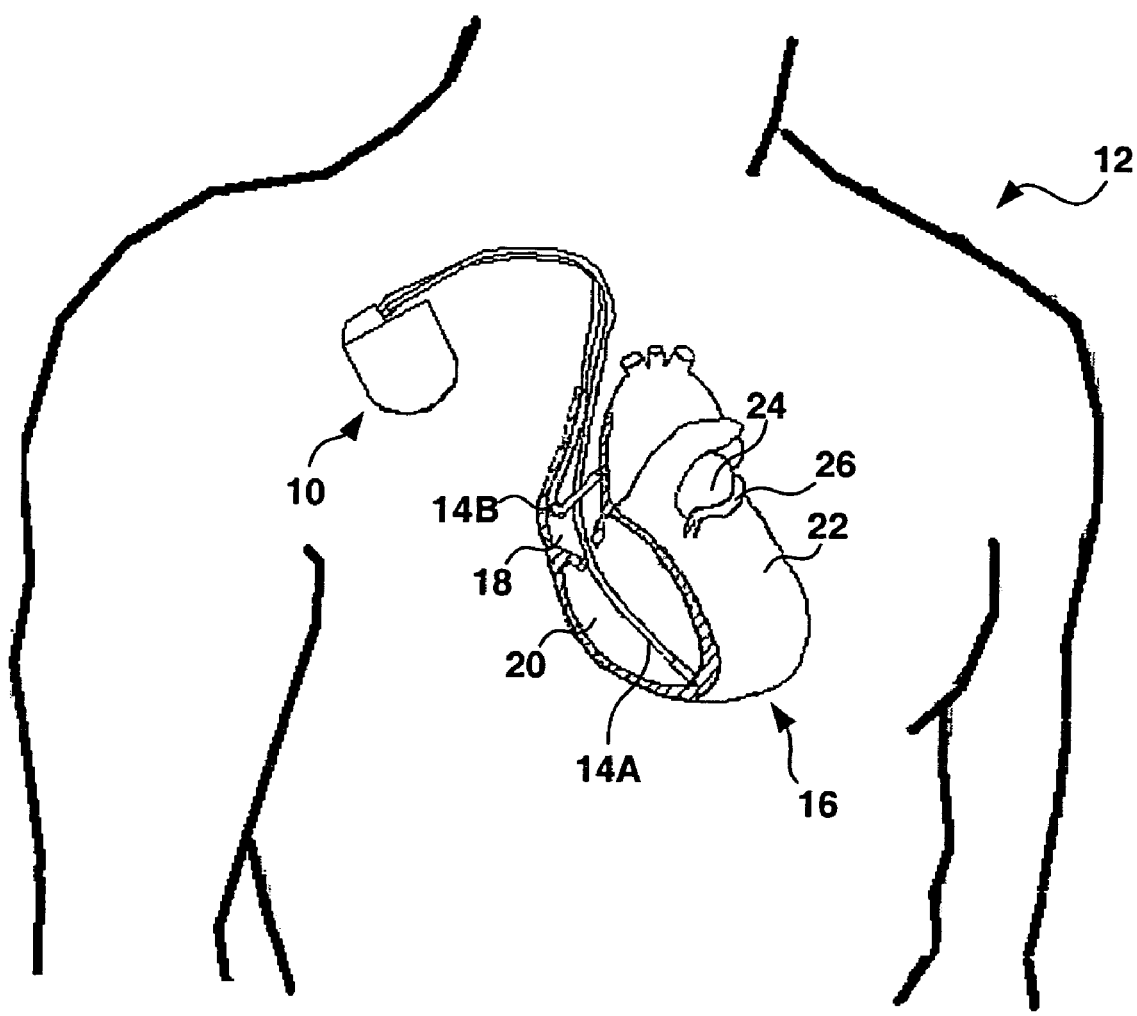
FIG. 1 is a conceptual diagram illustrating an example of an implanted medical device that detects degradation of an atrial myocardium implanted within a patient.

FIG. 1 is a conceptual diagram illustrating an example of an implanted medical device (IMD) 10 that detects degradation of an atrial myocardium implanted within a patient 12. In exemplary embodiments, IMD 10 takes the form of a multi-chamber cardiac pacemaker. In the exemplary embodiment illustrated in FIG. 1, IMD 10 is coupled to leads 14A and 14B (collectively "leads 14") that extend into the heart 16 of patient 12. More particularly, right ventricular (RV) lead 14A extends through one or more veins (not shown), the superior vena cava (not shown), and right atrium 18, and into right ventricle 20, and right atrial (RA) lead 14A extends through the veins and vena cava, and into the right atrium of heart 16.

IMD 10 senses electrical signals attendant to the depolarization and repolarization of heart 16 via electrodes (not shown) located on leads 14. In some embodiments, IMD 10 also provide pacing pulses via electrodes located on leads 14. The electrodes located on leads 14 are unipolar or bipolar, as is well known in the art.

As will be described in greater detail below, IMD 10 processes an atrial electrogram signal to detect degradation of the myocardium of atria 18 and 24. More particularly, IMD 10 measures at least one characteristic of P-waves within the signal and detects degradation of atrial myocardium based on changes in the characteristic over time. Exemplary characteristics of P-waves that are measured by IMD 10 include amplitudes, variability of widths, and dispersion of widths. In some embodiments, IMD 10 uses template-matching techniques known in the art to identify changes in P-wave morphology over time. In some embodiments, IMD 10 detects ischemia within atria 18 and 24, identifies a risk of angina resulting from an ischemic event within ventricles 20 and 22, and/or identifies a risk of future atrial fibrillation based on changes to the one or more P-wave characteristics measured.

In some embodiments, IMD 10 stores an indication of the detected or identified condition within a memory (not shown) for retrieval by a clinician using a programming device (not shown) via device telemetry. In some embodiments, IMD 10 alerts patient 12 to the potential danger posed by the detected degradation of the myocardium by activating an alarm (not shown). In such embodiments, IMD 10 allows degradation of atrial myocardium to be detected near onset, outside of a clinic setting, which can, in turn, lead to prompt diagnosis and treatment of the condition by a clinician. For example, detection of degradation of the myocardium could prompt a clinician to prescribe antiarrhythmia and/or anticoagulant medications in anticipation of a likelihood of future atrial fibrillation episodes.

In exemplary embodiments, IMD 10 also controls delivery of therapy to patient 12, e.g., initiates or modifies therapy, based on the detection of degradation of atrial myocardium. For example, in some embodiments, IMD 10 increases the aggressiveness of rate responsive atrial pacing via lead 14B in response to identification of a risk of future atrial fibrillation due to myocardial degradation. In such embodiments IMD 10 can increase the aggressiveness of rate responsive pacing by, for example, increasing the slope of a function used by IMD 10 to determine an atrial escape interval based on activity. The increased slope causes a greater percentage of atrial depolarizations to be paced, which can reduce the likelihood of occurrence of atrial fibrillation. Where IMD 10 paces one or both of ventricles 20 and 22 by tracking the atrial rate, some embodiments of IMD 10 also "decouple" the ventricular pacing rate from the atrial rate in response to identification of a risk of future atrial fibrillation due to myocardial degradation to avoid tracking the high and irregular atrial rates associated with atrial fibrillation.

In some embodiments, IMD 10 controls delivery of a drug by a drug delivery device (not shown) or neurostimulation therapy by a neurostimulator in response to detection of degradation of the atrial myocardium. For example, in some embodiments IMD 10 controls delivery of nitroglycerine or other drugs used to treat angina, or spinal cord stimulation used to treat angina, in response to a detection of increased risk to develop angina based on P-wave changes over time. Additionally, where IMD 10 paces one or both of ventricles 20 and 22 based on the atrial rate, some embodiments of IMD 10 decrease the maximum tracking rate for the ventricles in response to detection of increased risk to develop angina. High pacing rates during episodes of angina can prolong or increase the severity of such episodes. In some embodiments, IMD 10 detects ischemia based on P-wave changes, and controls delivery of thrombolytic drugs to heart 16.

The configuration of IMD 10 and leads 14 illustrated in FIG 1 is merely exemplary. In various embodiments, IMD 10 coupled to any number of leads 14 that extend to a variety of positions within or outside of heart 16. For example, in some embodiments, IMD 10 is coupled to a lead 14 that extends to a position within coronary sinus 26 near left ventricle 22 for left ventricular sensing and/or pacing. In some embodiments, at least some of leads 14 are epicardial leads.

Moreover, in some embodiments, IMD 10 does not include any leads 14 at all, but instead receives a signal that represents electrical activity within heart 16 via electrodes integral with a housing of IMD 10 (not shown). In such embodiments, IMD 10 takes the form of, for example, an implantable loop recorder. Further, in some embodiments, IMD 10 is not implanted within patient 12, but is instead coupled with subcutaneous leads 14 that extend through the skin of patient 12 to a variety of positions within or outside of heart 16, or transcutaneous leads that detect electrical activity within the heart from positions on the surface, e.g., skin, of patient.

Figure 2:
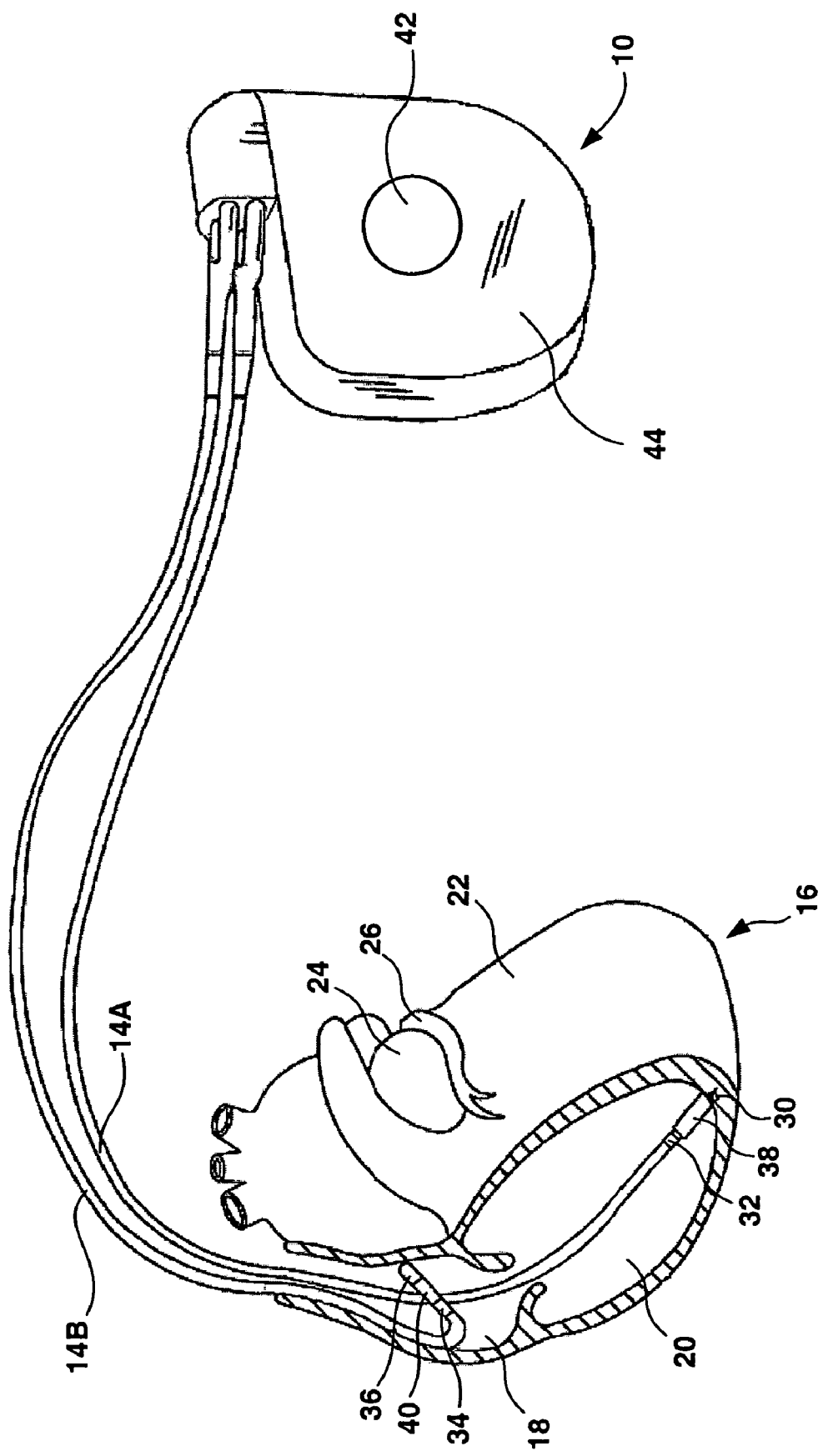
FIG. 2 is a conceptual diagram illustrating the implantable medical device of FIG. 1 and the heart of the patient in greater detail.

FIG. 2 is conceptual diagram further illustrating IMD 10 and heart 16 of patient 12. In exemplary embodiments, each of leads 14 includes an elongated insulative lead body carrying a number of concentric coiled conductors separated from one another by tubular insulative sheaths. Located adjacent a distal end of leads 14A and 14B are bipolar electrodes 30 and 32, and 34 and 36, respectively. In exemplary embodiments, electrodes 32 and 34 take the form of ring electrodes, and electrodes 30 and 36 take the form of extendable helix tip electrodes mounted retractably within insulative electrode heads 38 and 40, respectively. Each of the electrodes 30-36 is coupled to one of the coiled conductors within the lead body of its associated lead 14.

Sense/pace electrodes 30-36 sense electrical signals attendant to the depolarization and repolarization of heart 16. The electrical signals are conducted to IMD 10 via leads 14. In exemplary embodiments, at least some of sense/pace electrodes 30-36 further deliver pacing to cause depolarization of cardiac tissue in the vicinity thereof. In some embodiments, IMD 10 also includes one or more indifferent housing electrodes, such as housing electrode 42, formed integral with an outer surface of the hermetically sealed housing 44 of IMD 10. In such embodiments, any of electrodes 30-36 are capable of being used for unipolar sensing or pacing in combination with housing electrode 42.

Figure 3:
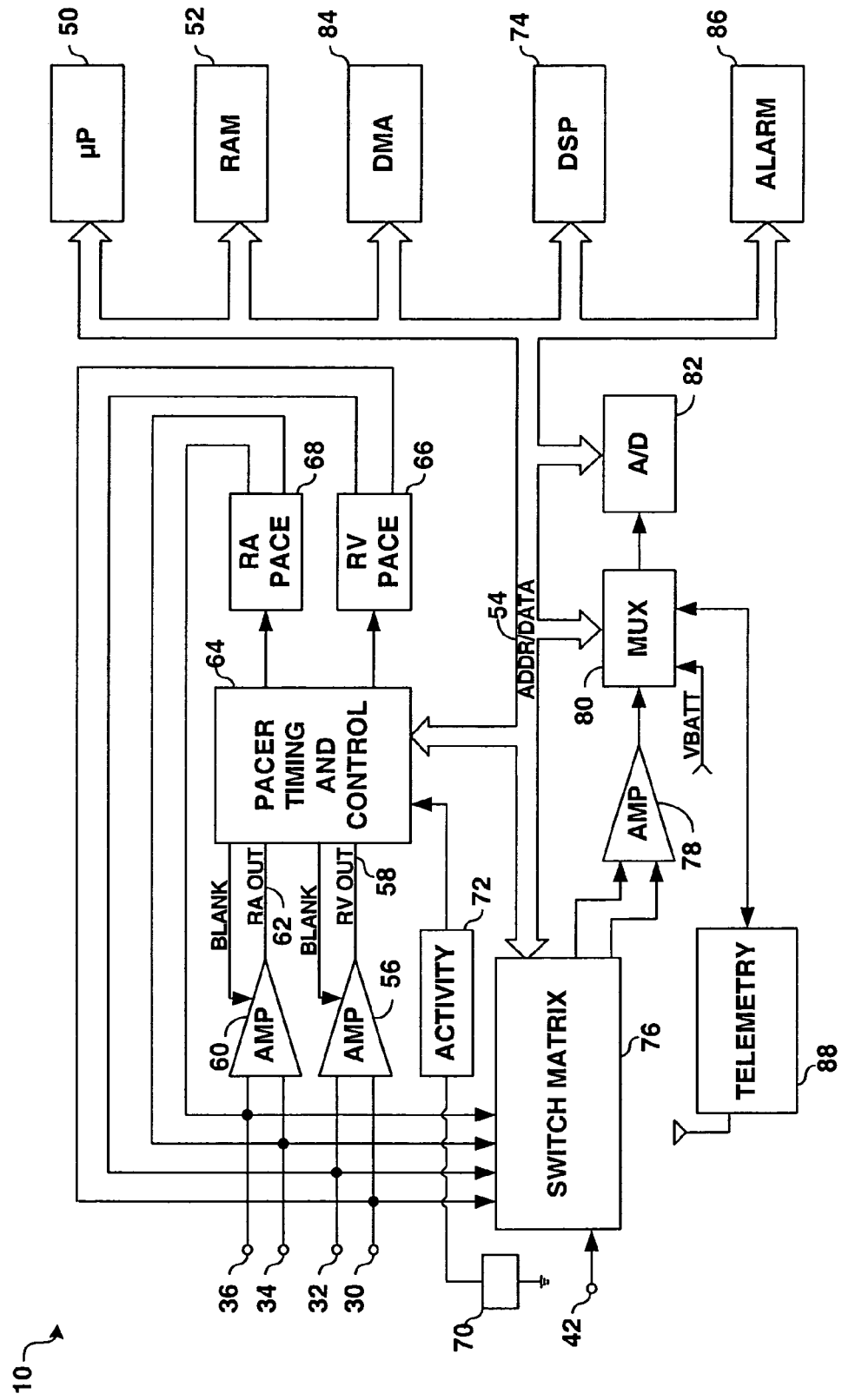
FIG. 3 is a functional block diagram illustrating the implantable medical device of FIG. 1 in greater detail.

FIG. 3 is a functional block diagram of IMD 10. In the illustrated embodiment, IMD 10 takes the form of a multi-chamber pacemaker having a microprocessor-based architecture. However, this diagram should be taken as exemplary of the type of device in which various embodiments of the present invention may be embodied, and not as limiting. For example, some embodiments of the invention provide no pacing therapy, or any therapy at all. An example of such an embodiment is an implantable loop recorder.

IMD 10 includes a microprocessor 50. Microprocessor 50 executes program instructions stored in memory, such as a ROM (not shown), EEPROM (not shown), and/or RAM 52, which control microprocessor 50 to perform the functions ascribed to microprocessor 50 herein. Microprocessor 50 is coupled to, e.g., communicates with and/or controls, various other components of IMD 10 via an address/data bus 54.

Electrodes 30 and 32 are coupled to amplifier 56, which takes the form of an automatic gain controlled amplifier providing an adjustable sensing threshold as a function of the measured R-wave amplitude. A signal is generated on RV out line 58 whenever the signal sensed between electrodes 30 and 32 exceeds the present sensing threshold. Electrodes 34 and 36 are coupled to amplifier 60, which also takes the form of an automatic gain controlled amplifier providing an adjustable sensing threshold as a function of measured P-wave amplitude. A signal is generated on RA out line 62 whenever the signal sensed between electrodes 34 and 36 exceeds the present sensing threshold.

In some embodiments, IMD 10 paces heart 16. Pacer timing/control circuitry 64 includes programmable digital counters which control the basic time intervals associated with modes of pacing. Circuitry 64 also controls escape intervals associated with pacing. In the exemplary two-chamber pacing environment, pacer timing/control circuitry 64 controls the atrial and ventricular escape intervals that are used to time pacing pulses delivered to right atrium 18 and right ventricle 20.

Intervals defined by pacer timing/control circuitry 64 also include the refractory periods during which sensed R-waves and P-waves are ineffective to restart timing of the escape intervals, and the pulse widths of the pacing pulses. The durations of these intervals are determined by microprocessor 50 in response to data stored in RAM 52, and are communicated to circuitry 64 via address/data bus 54. Pacer timing/control circuitry 64 also determines the amplitude of the cardiac pacing pulses under control of microprocessor 50.

Microprocessor 50 operates as an interrupt driven device, and is responsive to interrupts from pacer timing/control circuitry 64 corresponding to the occurrence of sensed P-waves and R-waves and corresponding to the generation of cardiac pacing pulses. Those interrupts are provided via data/address bus 54. Any necessary mathematical calculations to be performed by microprocessor 50 and any updating of the values or intervals controlled by pacer timing/control circuitry 64 take place following such interrupts.

In accordance with the selected mode of pacing, pacer timing/control circuitry 64 triggers generation of pacing pulses by one or more of pacer output circuits 66 and 68, which are coupled to electrodes 30 and 32, and 34 and 36, respectively. Output circuits 66 and 68 are pulse generation circuits known in the art, which include capacitors and switches for the storage and delivery of energy as a pulse. Pacer timing/control circuitry 64 resets escape interval counters upon detection of R-waves or P-waves, or generation of pacing pulses, and thereby controls the basic timing of cardiac pacing functions.

As indicated above, in some embodiments IMD 10 provides rate-responsive pacing therapy to patient 12. IMD 10 is shown in FIG. 3 as including an activity sensor 70. Activity sensor 70 typically (although not necessarily) provides a sensor output that varies as a function of a measured parameter relating to metabolic requirements of patient 12. In exemplary embodiments, activity sensor 70 is a piezoceramic accelerometer bonded to a hybrid circuit located inside housing 44 (FIG. 2), or electrodes to detect respiration rate of patient 12 via cyclical variations in the thoracic impedance of patient 12.

The output signal provided by activity sensor 86 is coupled to an activity detection circuit 72, which determines the activity level, e.g., counts, of patient 12 based on the output. The activity level or counts are provided to pacer timing/control circuit 64, which adjusts one or more escape intervals based on the activity level or counts to provide rate-responsive pacing. In some embodiments, IMD 10 includes multiple activity sensors 70, and provides rate-responsive pacing based on a combination or blending of the outputs of the various sensors. In some embodiments, microprocessor 50 measures activity based on the length of detected QT intervals within electrical signals received from combinations of electrodes 30-36 and 42, which vary based on activity, and in effect act as an activity sensor. In such embodiments, microprocessor 50 provides an indication of the activity level to circuitry 64 for adjustment of one or more escape intervals.

As indicated above, in some embodiments IMD 10 times delivery of pacing pulses to right ventricle 20 via electrodes 30 and 32 based on the occurrence of paced or intrinsic atrial depolarizations, e.g., according to an atrial-tracking pacing mode. In such embodiments, pacer timing/control circuitry 64 sets a ventricular escape interval upon receipt of a signal on RA out line 62. In some embodiments, the ventricular escape interval, e.g., the atrial-tracking rate, is constrained by maximums and minimums provided to circuitry 64 by microprocessor 50.

As mentioned above, IMD 10 receives an atrial electrogram signal that represents electrical activity within heart 16, processes the signal to measure at least one characteristic of P-waves within the signal, and detects degradation of the atrial myocardium based on changes in the measured characteristics over time. In exemplary embodiments, the signal is digitally processed by a digital signal processor (DSP) 74 for measurement of the characteristics of the signal. In such embodiments, switch matrix 76 is used to select which of electrodes 30-32 and 42 are coupled to wide band (0.5-200 Hz) amplifier 78 for use in digital signal analysis. Selection of electrodes is controlled by microprocessor 60 via data/address bus 66, and the selections may be varied as desired.

The analog atrial electrogram signal derived from the selected electrodes and amplified by amplifier 78 is provided to multiplexer 80, and thereafter converted to a multi-bit digital signal by A/D converter 82. In exemplary embodiments, DSP 74 processes the multi-bit digital signal to measure P-wave amplitudes and/or widths, as will be described in greater detail below. In some embodiments, the digital signal is stored in RAM 52 under control of direct memory access circuit 84 for later analysis by DSP 74. The P-wave amplitudes and/or widths measured by DSP 74 are stored in RAM 52, where they are retrieved by microprocessor 60 for analysis. Based on an analysis of the amplitudes, variability of the widths, and/or dispersions of the widths, which will be described in greater detail below, microprocessor 50 detects degradation of the atrial myocardium.

Although IMD 10 is described herein as having separate processors, microprocessor 50 may perform both the functions ascribed to it herein and digital signal analysis functions ascribed to DSP 74 herein. Moreover, although described herein in the context of microprocessor based pacemaker embodiment IMD 10, the invention may be embodied in various implantable medical devices that include one or more processors, which may be microprocessors, DSPs, FPGAs, or other digital logic circuits.

Further, in some embodiments, IMD 10 does not utilize digital signal analysis to measure P-wave amplitudes and/or widths. In such embodiments, IMD 10 includes analog peak, slope or threshold detecting amplifier circuits to identify the peaks and/or beginning and end points of P-waves, as is known in the art. Further, in such embodiments, pacer timing/control circuit 64 receives the output of these amplifier circuits, and provides an indication of the occurrence of these events to microprocessor 50 so that microprocessor 50 is able to determine the P-wave amplitudes and/or widths.

In some embodiments, microprocessor 50 provides an indication of the detection of degradation of the atrial myocardium to patient 12. In exemplary embodiments, IMD 10 includes an alarm 86 that provides an audible signal to patient 12 in whom IMD 10 is implanted. By activating alarm 86, microprocessor 50 alerts patient 12 to a possible problem that requires consultation with a clinician.

In some embodiments, IMD 10 is programmable by means of an external programming unit (not shown), and certain features of IMD 10 are controlled by a patient activator (not shown). Both the programming unit and the patient activator communicate with IMD 10 via telemetry circuit 88 using RF telemetry techniques known in the art. In exemplary embodiments, microprocessor 50 stores an indication of detected degradation of the atrial myocardium in RAM 52, and provides the indication to either patient 12 or a clinician when interrogated by a patient activator or programmer via a telemetry circuit 88. In some embodiments, microprocessor 50 also stores diagnostic data, such as P-wave amplitudes, widths, variability of widths, dispersions of widths, and samples of the atrial electrogram signal. Such information is provided to a clinician via telemetry circuit 88 and the programmer, and can be displayed by the programmer in variety of graphical forms, such as charts, graphs, histograms, EGM strips with marker channel information, or the like.

In exemplary embodiments, microprocessor 50 controls delivery of therapies to patient 12 based on the P-wave amplitudes, variabilities of the P-wave widths, and/or dispersions of the P-wave widths. In some embodiments, microprocessor 50 increases the aggressiveness of rate responsive atrial pacing to increase the percentage of atrial depolarizations that are paced. In such embodiments, microprocessor 50 provides circuitry 64 with new rate-response parameters or functions, e.g., increases the slope of one or more rate response functions, to increase the aggressiveness of rate-responsive pacing.

In some embodiments, microprocessor 50 directs circuitry 74 to decouple the ventricular pacing rate from the atrial rate, e.g., or provides circuitry 74 a lower maximum atrial-tracking rate for ventricular pacing. Further, in some embodiments, microprocessor 50 controls delivery of one or more drugs or neurostimulation therapy by a drug delivery device or neurostimulator, respectively.

Figure 4:
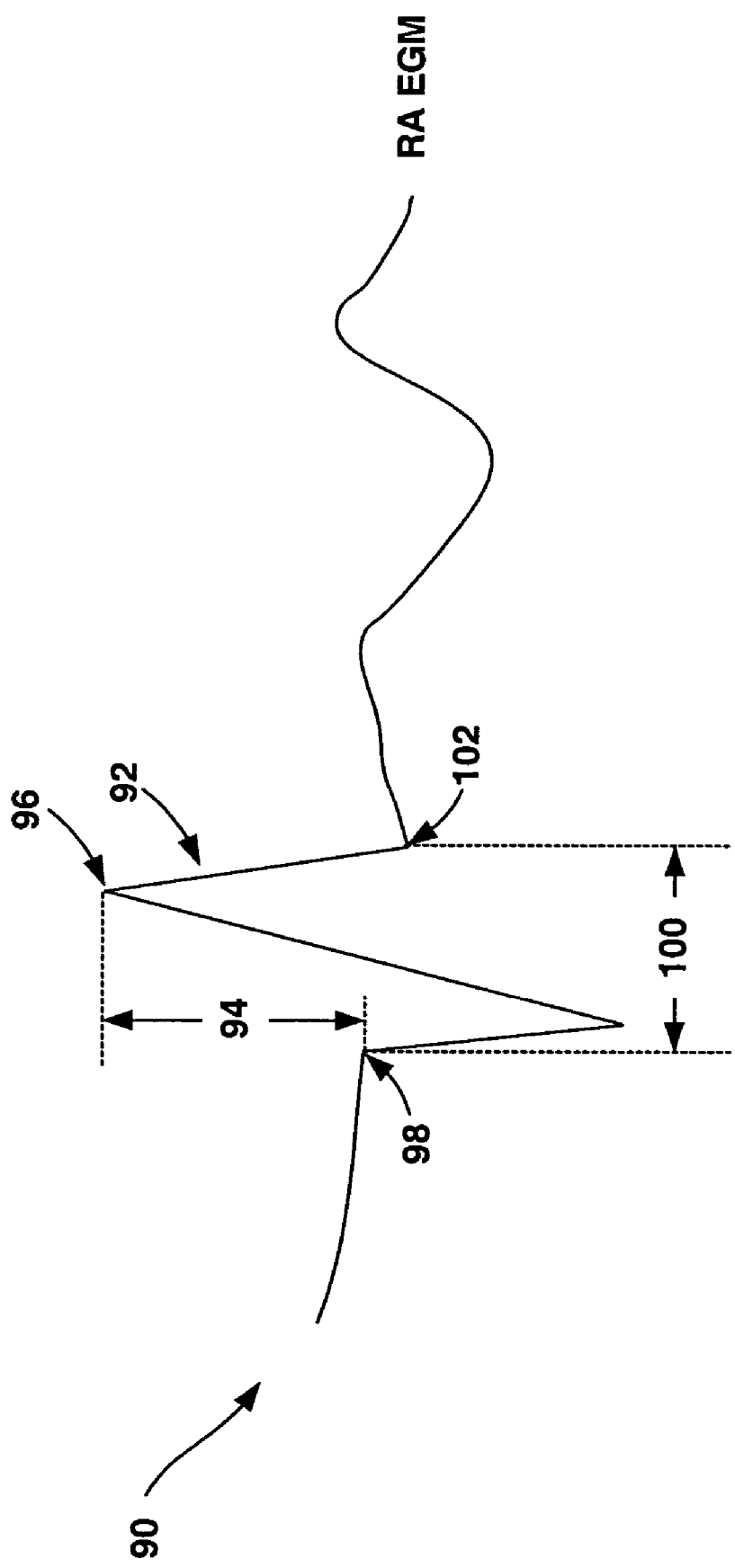
FIG. 4 is a timing diagram illustrating an example atrial electrogram signal processed by the implantable medical device of FIG. 1 to detect degradation of the atrial myocardium.

FIG. 4 is a timing diagram illustrating an example atrial electrogram signal 90 processed by IMD 10 to detect degradation of the atrial myocardium. Signal 90 is detected using electrodes 34 and 36 of RA lead 14B in a bipolar configuration, or one of electrodes 34 and 36 and housing electrode 42 in a unipolar configuration. In some embodiments, an electrogram signal is detected using two or more housing electrodes 42, enabling embodiments of IMD 10 that do not include leads, such as implantable loop recorder embodiments of IMD 10

Signal 90 includes a P-wave 92. In some embodiments, IMD 10 processes signal 90 to measure an amplitude 94 of P-wave 92, and/or a width 100 of P-wave 92. In exemplary embodiments, DSP 74 of IMD 10 digitally processes signal 90 to measure amplitude 94 and/or width 100. In some embodiments, IMD 10 compares multiple features of P-wave 92 to a template stored in a memory, such as RAM 52.

For ease of illustration, only a portion of signal 90 representing a single cardiac cycle of heart 16 is shown in FIG. 4. However, it is understood that DSP 74 measures multiple amplitudes 94 and/or widths 100 within signal 90, or compares multiple P-waves 92 to a template, over time. DSP 74 provides microprocessor 50 with the measured values, as described above, and/or indicates inadequate similarity of a P-wave 92 to the template to microprocessor.

As it is known in the art, the atrial EGM comprises the wave (not shown) representative of ventricular depolarization, which is synchronous in time with the QRS wave of a surface ECG. When sensed via a combination of electrodes 34, 36 and 42, this wave is referred to as a "far-field" R-wave. The amplitude of the far-field R-wave depends of the distance between the electrodes and the orientation of an axis of lead 14B relative to the ventricular mass.

In order to measure amplitude 94 and/or width 100 of P-wave 92, or to compare P-wave 92 to a template, DSP 74 first identifies P-wave 92 within signal 90. DSP 74 identifies P-wave 92 within signal 90 by any method known in the art. In some embodiments, DSP 74 receives an indication of the occurrence of P-wave 92 from pacer timing/control circuit 64. In other embodiments, DSP 74 identifies P-wave 92 by detecting a number of threshold-crossings of the signal 90 or zero-crossings of the first derivative of signal 90 occurring within a time window. In some embodiments, DSP 74 detects P-wave 92 using techniques described in commonly assigned U.S. Pat. No. 6,029,087, to Wohlgemuth, and titled "Cardiac Pacing System With Improved Physiological Event Classification Based on DSP."

DSP 74 measures amplitude 94 as the value of the digital signal at peak 96, which is positive or negative depending on the polarity of signal 90. DSP 74 measures width 100 as the period of time from beginning point 98 to ending points 102 of P-wave 92. In exemplary embodiments, DSP 100 identifies beginning point 98 and ending points 102 as threshold-crossings of the digital signal or zero-crossings of the first derivative of the digital signal.

Figure 5:
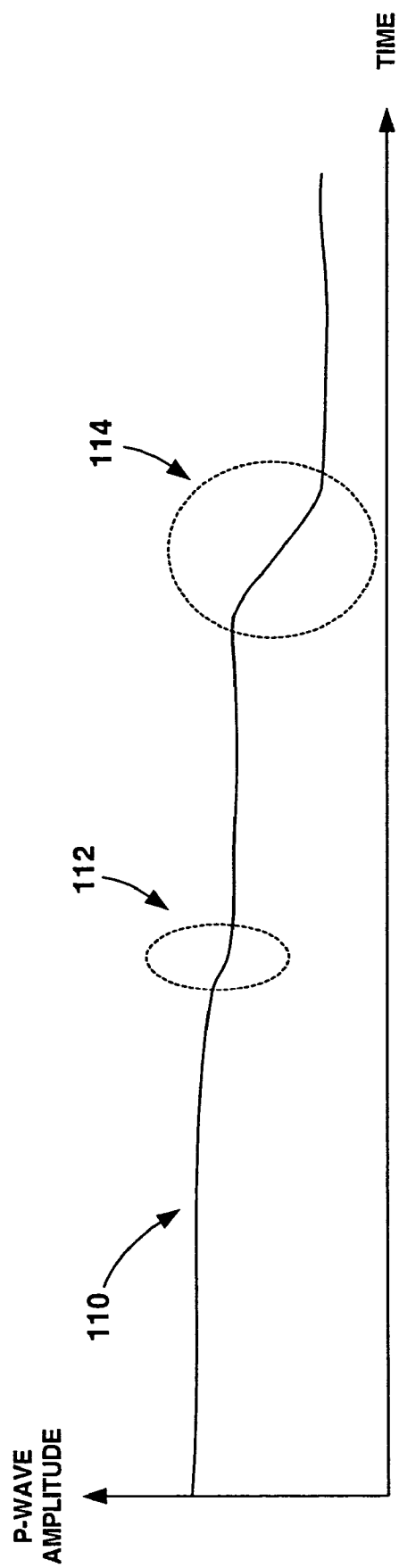
FIG. 5 is a graph illustrating P-wave amplitude over time.

FIG. 5 depicts a curve 110 that represents P-wave amplitudes 94 measured by DSP 74 over time. Decreased P-wave amplitudes 94 are indicative of degradation of the atrial myocardium. Medically significant changes in P-wave amplitudes 94, e.g., those that indicate degradation of the atrial myocardium, are likely to occur and be noticeable over a period of months, while less significant changes will occur beat-to-beat. Consequently, in exemplary embodiments, microprocessor 50 determines average values of P-wave amplitude over periods of time, e.g. averages for days, weeks, or months, and compares a current average to a previous average to detect degradation of the atrial myocardium.

Further, in some embodiments, relatively small long term decreases in P-wave amplitude, such as that depicted in region 112 of curve 110, are not considered significant, while larger long term decreases, such as that depicted in region 114, are considered significant. Consequently, the previous average P-wave amplitude that microprocessor 50 compares a current average P-wave amplitude to need not be the average for the immediately preceding period. By comparing the current average P-wave value from a more distantly previous average, microprocessor 50 can better identify the magnitude of long-term changes in P-wave amplitude. In exemplary embodiments, microprocessor 50 compares the difference between or ratio of the current and past average P-wave values to a threshold stored in a memory, such as RAM 52.

Figure 6:
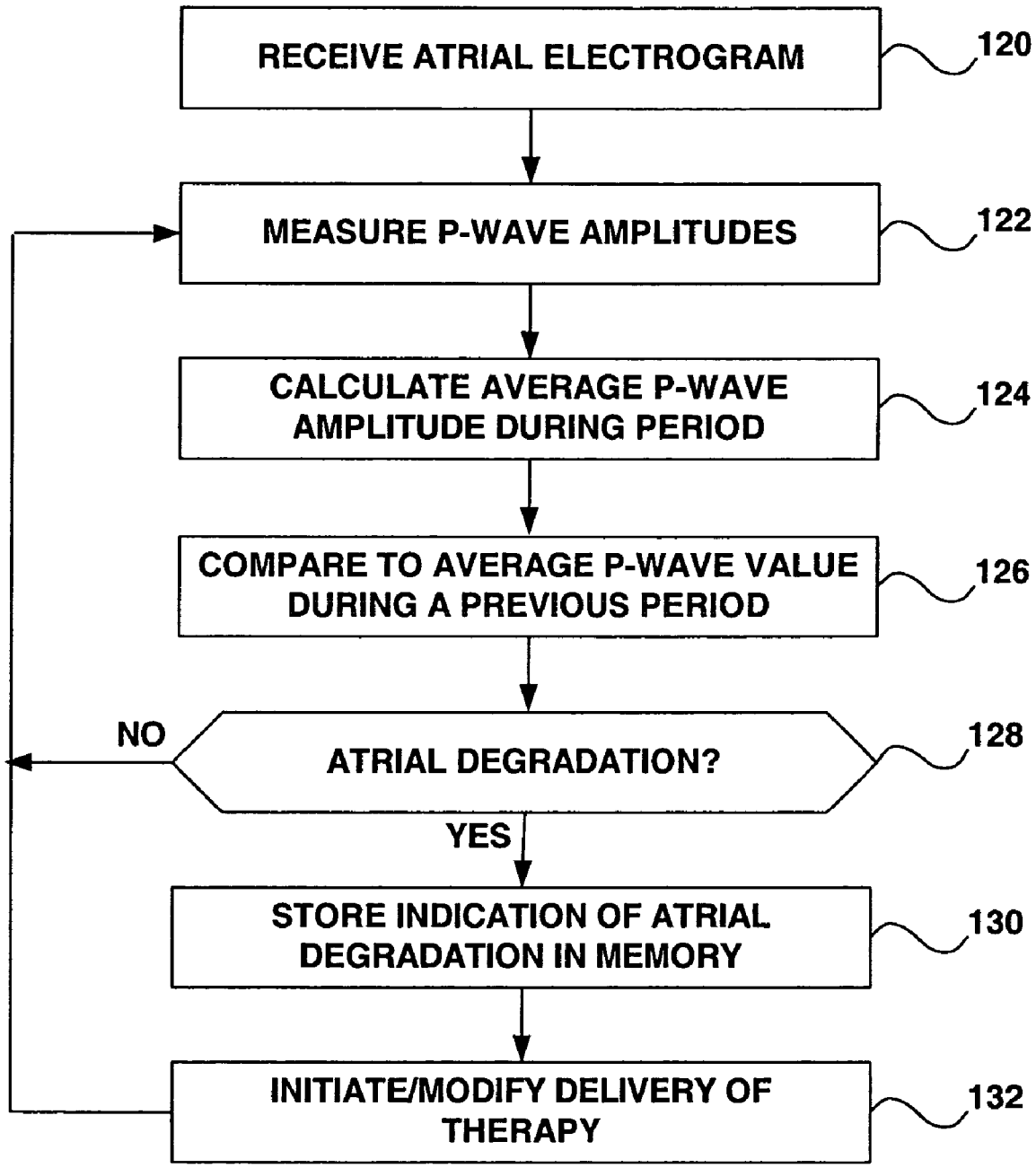
FIG. 6 is a flow diagram illustrating an exemplary mode of operation of the implantable medical device of FIG. 1 to detect degradation of the atrial myocardium based on P-wave amplitudes over time.

FIG. 6 is a flow diagram illustrating an exemplary mode of operation of IMD 10 to detect degradation of the atrial myocardium based on P-wave amplitudes over time. DSP 74 receives atrial electrogram signal 90 via A/D converter 82 (120), and measures amplitudes 94 of P-waves 92 therein (122). In some embodiments, DSP 74 does not measure amplitudes 94 continuously, but instead samples amplitudes periodically.

Microprocessor 50 receives amplitudes 94 from DSP 74, and calculates an average value of the amplitudes over a current period of time (124). Microprocessor 50 compares the current average value to a previous average value, which in some embodiments is not an immediately preceding average value (126). Microprocessor 50 detects degradation of the atrial myocardium based on the comparison (128). In exemplary embodiments, microprocessor 50 compares the difference between or ratio of the current and previous average values to a threshold value stored in RAM 52.

In some embodiments, if microprocessor 50 detects degradation of the atrial myocardium, microprocessor 50 stores an indication of the detection within a memory (130), activates an alarm, and/or initiates or modifies delivery of a therapy (132), as described above. For example, in some embodiments microprocessor 50 provides a new rate response function to pacer timing control circuit 64, as described above. As illustrated in FIG. 6, DSP 74 continues to measure P-wave amplitudes, and microprocessor calculates averages of the measured amplitudes over periods of time after both detection and non-detection of degradation of the atrial myocardium.

Figure 7:
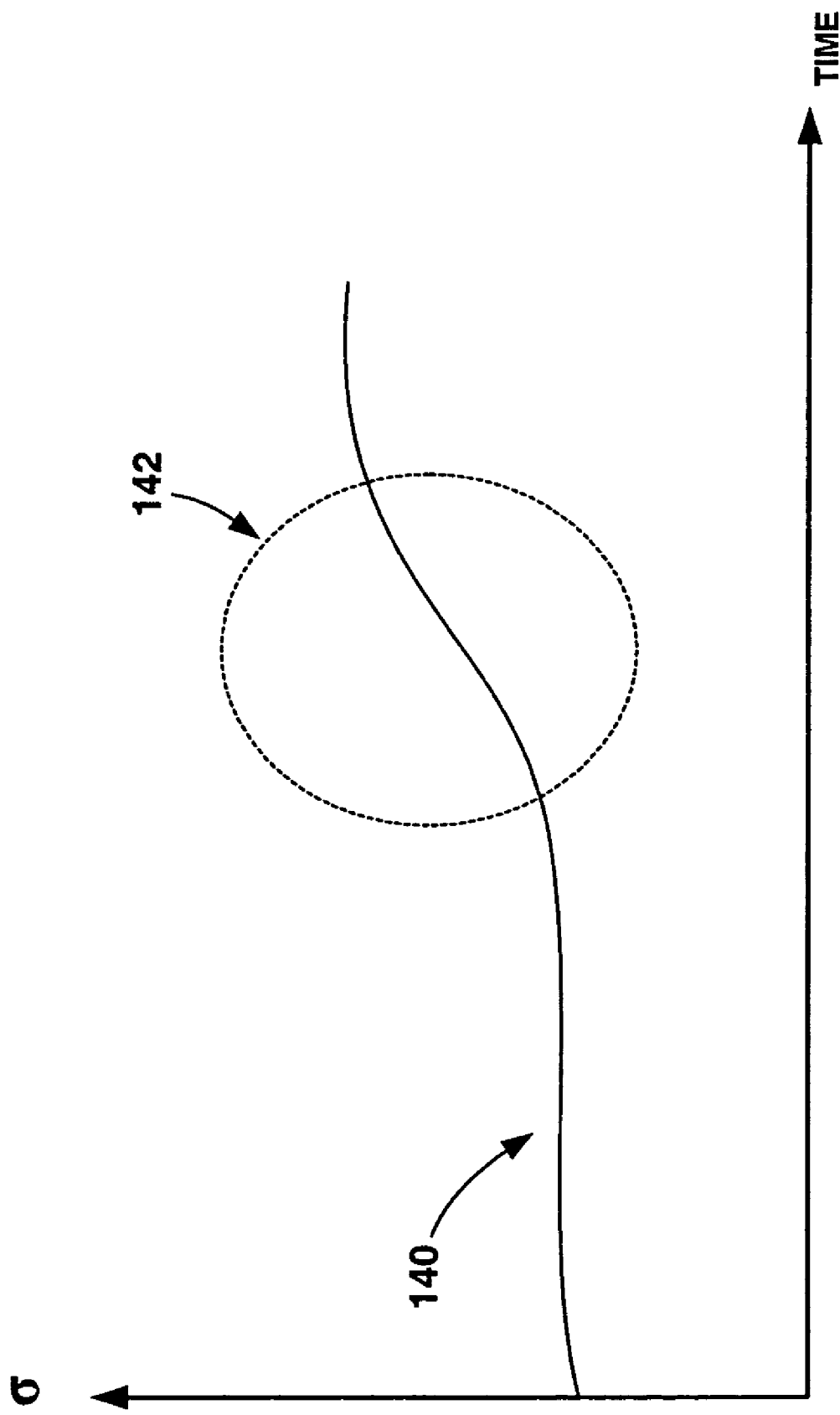
FIG. 7 is a graph illustrating variability of P-wave widths over time.

FIG 7 depicts a curve 140 that illustrates variability of P-wave widths 100 measured by DSP 74 over time. Degradation of the atrial myocardium, particularly that caused by dilation of the atria 18 and 24 (FIG. 1), leads to increased variability of the widths 100 of P-waves 92, such as that indicated in region 142 of curve 140. As was the case with the determination of average P-wave amplitudes, microprocessor 50 determines the variabilities of P-wave widths 100 measured over relatively long periods of time, e.g. averages for days, weeks, or months, and compares a variability for a current period of time to the variability of a previous period of time to detect degradation of the atrial myocardium. Further, in some embodiments, microprocessor 50 compares variability P-wave widths 100 for the current period to a variability of P-waves widths 100 measured a number of periods before to better recognize the magnitude of long-term changes in P-wave width variability. In exemplary embodiments, microprocessor 50 compares the difference between or ratio of the variabilities for current and past time periods to a threshold stored in a memory, such as RAM 52.

Figure 8:
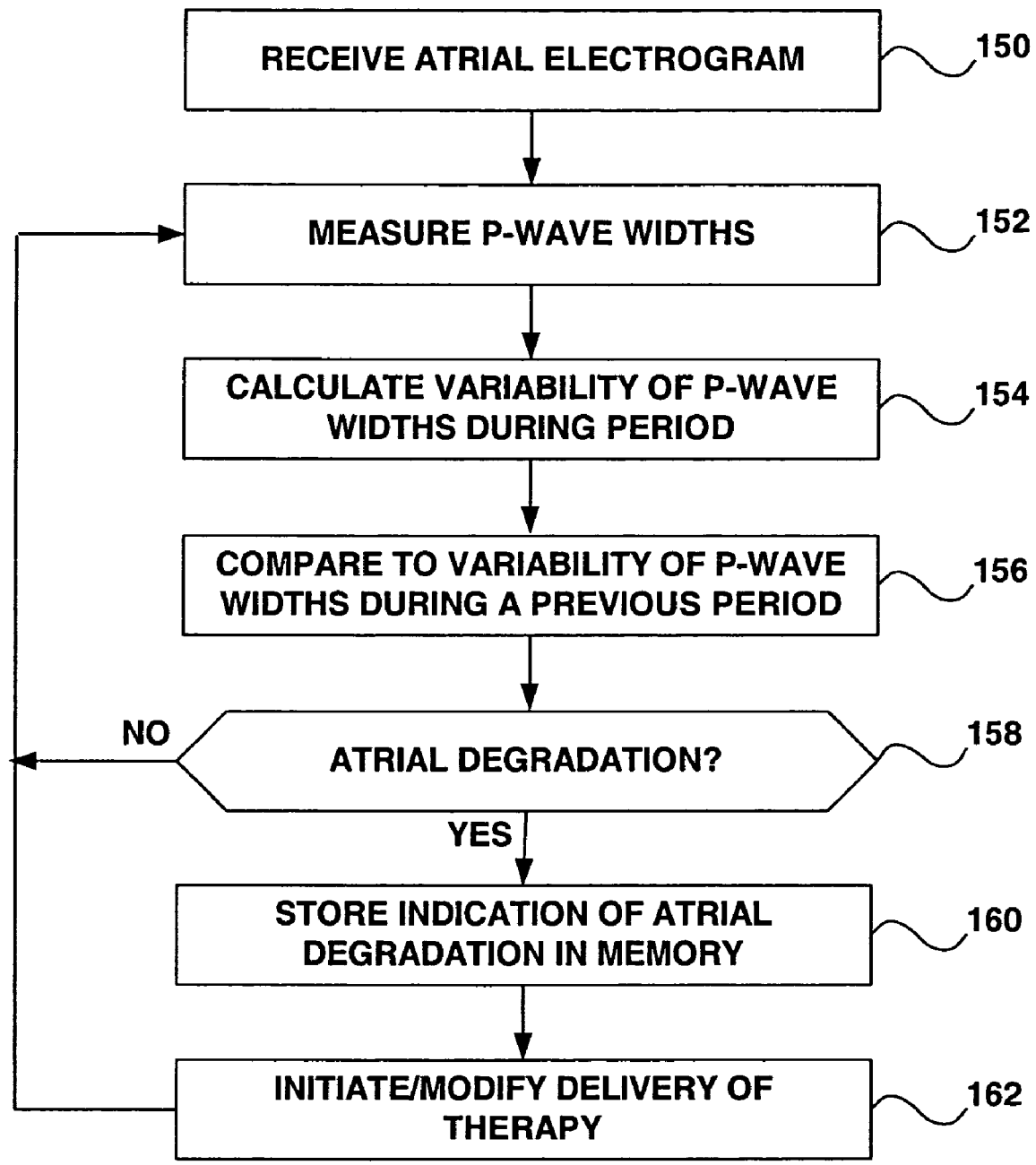
FIG. 8 is a flow diagram illustrating an exemplary mode of operation of the implantable medical device of FIG. 1 to detect degradation of the atrial myocardium based on variability of P-wave widths over time.

FIG. 8 is a flow diagram illustrating an exemplary mode of operation of IMD 10 to detect degradation of the atrial myocardium based on variability of P-wave widths 100 over time. DSP 74 receives atrial electrogram signal 90 via A/D converter 82 (150), and measures widths 100 of P-waves 92 therein (152). In some embodiments, DSP 74 does not measure widths 100 continuously, but instead samples P-wave widths 100 periodically. By measuring widths 100 of P-waves 92 periodically, IMD 10 conserves the processing resources of DSP 74 and a battery of IMD 10 used to provide power to DSP 74

Microprocessor 50 receives measured widths 100 from DSP 74, and calculates a variability of the widths over a current period of time (154). Microprocessor 50 compares the current variability to a previous variability, which in some embodiments is not the P-wave variability for the immediately preceding time period (156). Microprocessor 50 detects degradation of the atrial myocardium based on the comparison (158). In exemplary embodiments, microprocessor 50 compares the difference between or ratio of the current and previous variability values to a threshold value stored in RAM 52. In some embodiments, if microprocessor 50 detects degradation of the atrial myocardium, microprocessor 50 stores an indication of the detection within a memory (160), activates an alarm, and/or initiates or modifies delivery of a therapy (162), as described above.

Figure 9:
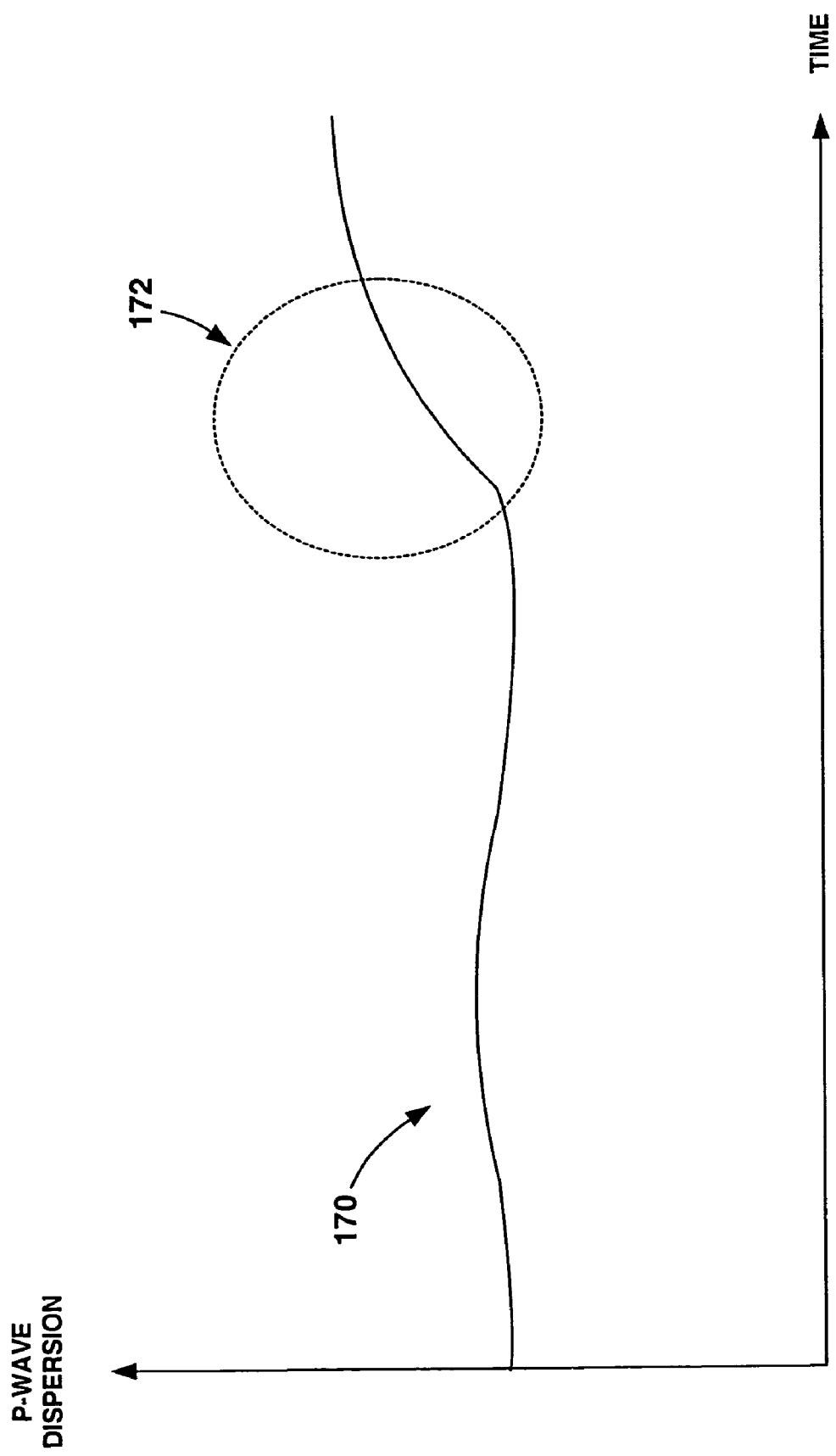
FIG. 9 is a graph illustrating dispersions of P-wave widths over time.

FIG. 9 depicts a curve 170 that illustrates dispersions of P-wave widths 100 measured by DSP 74 over time. A dispersion of P-wave widths 100 over a period of time is defined as the difference between the greatest and smallest P-wave widths 100 measured during that period. Long term increases in the dispersions of P-waves widths 100, e.g., over a number of months, indicate degradation of the atrial myocardium, while short-term increases, e.g., over a number of minutes, are indicative of an increased probability that angina will occur. Thus region 172 of curve 170 could be said to represent either degradation of the atrial myocardium or an impending episode of angina depending on the time-scale of the horizontal axis of FIG. 9.

In various embodiments, microprocessor 50 detects either or both of degradation of the atrial myocardium and impending angina by comparing a P-wave width dispersion calculated for a current period of time to a P-wave width dispersion calculated for a previous time. However, the lengths of the periods of time and the recentness of the P-wave dispersion a current P-wave dispersion is compared to varies depending on which condition is detected. In exemplary embodiments, microprocessor 50 compares the difference between or ratio of the dispersions for current and past time periods to a threshold stored in a memory, such as RAM 52.

Figure 10:
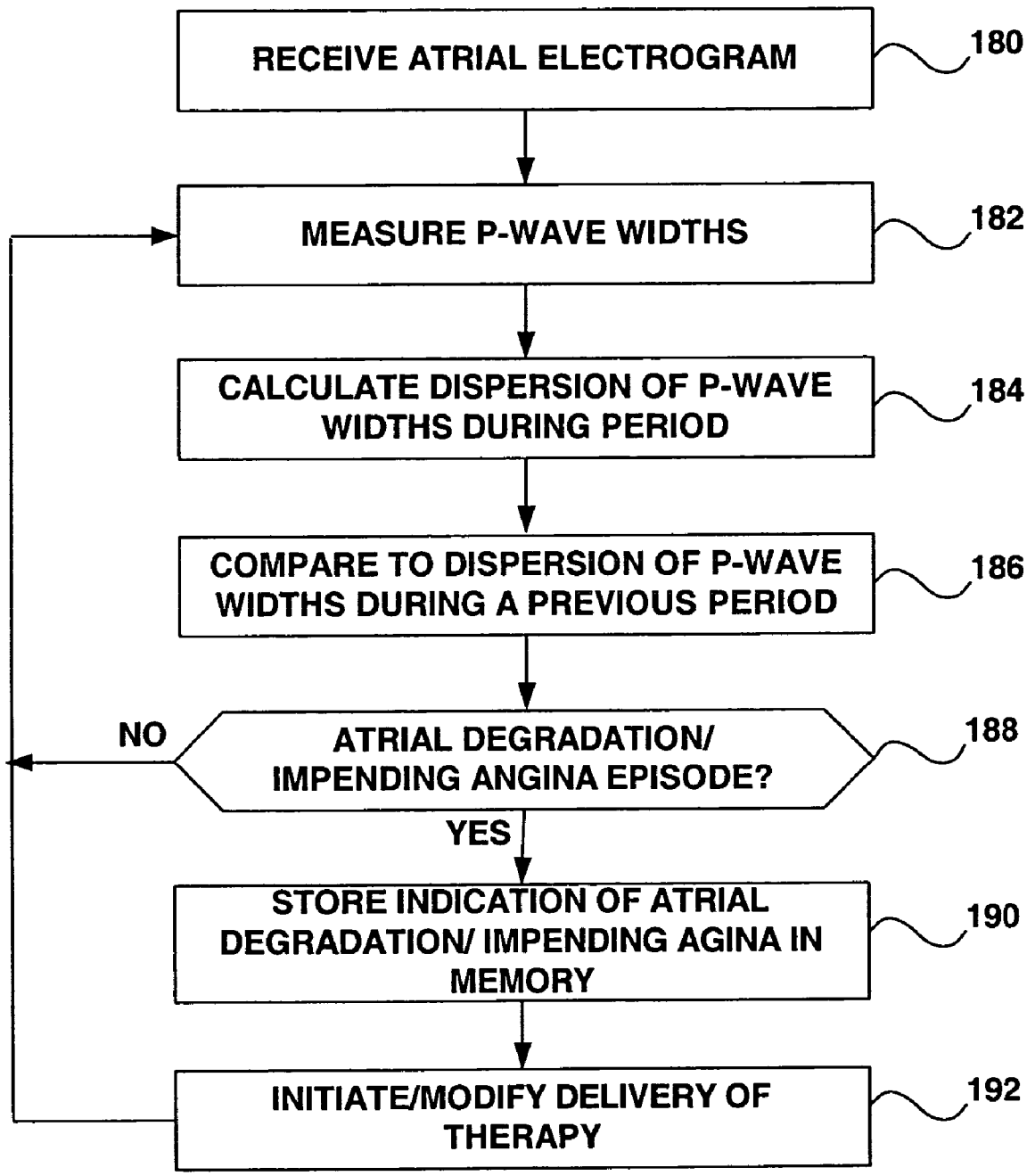
FIG. 10 is a flow diagram illustrating an exemplary mode of operation of the implantable medical device of FIG. 1 to detect degradation of the atrial myocardium or angina based on dispersions of P-wave widths over time.

FIG. 10 is a flow diagram illustrating an exemplary mode of operation of IMD 10 to detect degradation of the atrial myocardium or impending angina based on dispersions of P-wave widths 100 measured by DSP 74 over time. DSP 74 receives atrial electrogram signal 90 via A/D converter 82 (180), and measures widths 100 of P-waves 92 therein (182). As indicated above, in some embodiments, DSP 74 does not measure widths 100 continuously, but instead samples P-wave widths 100 periodically.

Microprocessor 50 receives measured widths 100 from DSP 74, and calculates a dispersion of the widths 100, e.g., a difference between the maximum and minimum widths 100 measured by DSP 74, over a current period of time (184). Microprocessor 50 compares the current dispersion to a previous dispersion (186), and detects degradation of the atrial myocardium or impending angina based on the comparison (188). In exemplary embodiments, microprocessor 50 compares the difference between or ratio of the current and previous dispersion values to a threshold value stored in RAM 52.

In some embodiments where microprocessor 50 detects impending angina based on the comparison, microprocessor 50 confirms the detection by determining whether QT intervals in a ventricular electrogram signal have shortened and/or whether an activity level indicated by activity monitor 72 has increased during the same period. Shortened QT intervals are caused by either physical or emotional stress and increased activity detected by activity sensor 70 is caused by physical stress. When a patient is in stress, there is an increased probability of the occurrence of an episode of angina. In embodiments where QT intervals are measured, DSP 74 receives a sampled ventricular electrogram signal and measures the QT intervals using techniques known in the art.

In some embodiments, if microprocessor 50 detects degradation of the atrial myocardium or angina, microprocessor 50 stores an indication of the detection within a memory (190), activates an alarm, and/or initiates or modifies delivery of a therapy (192), as described above. For example, in some embodiments where microprocessor 50 detects degradation of the atrial myocardium, microprocessor 50 increases the aggressiveness of rate responsive atrial pacing and/or decouples a ventricular pacing rate from the atrial rate, as described above. In some embodiments where microprocessor 50 detects angina, microprocessor 50 decreases a maximum atrial-tracking rate for ventricular pacing, and/or controls delivery of a drug or neurostimulation as will be described in greater detail below.

Figure 11:
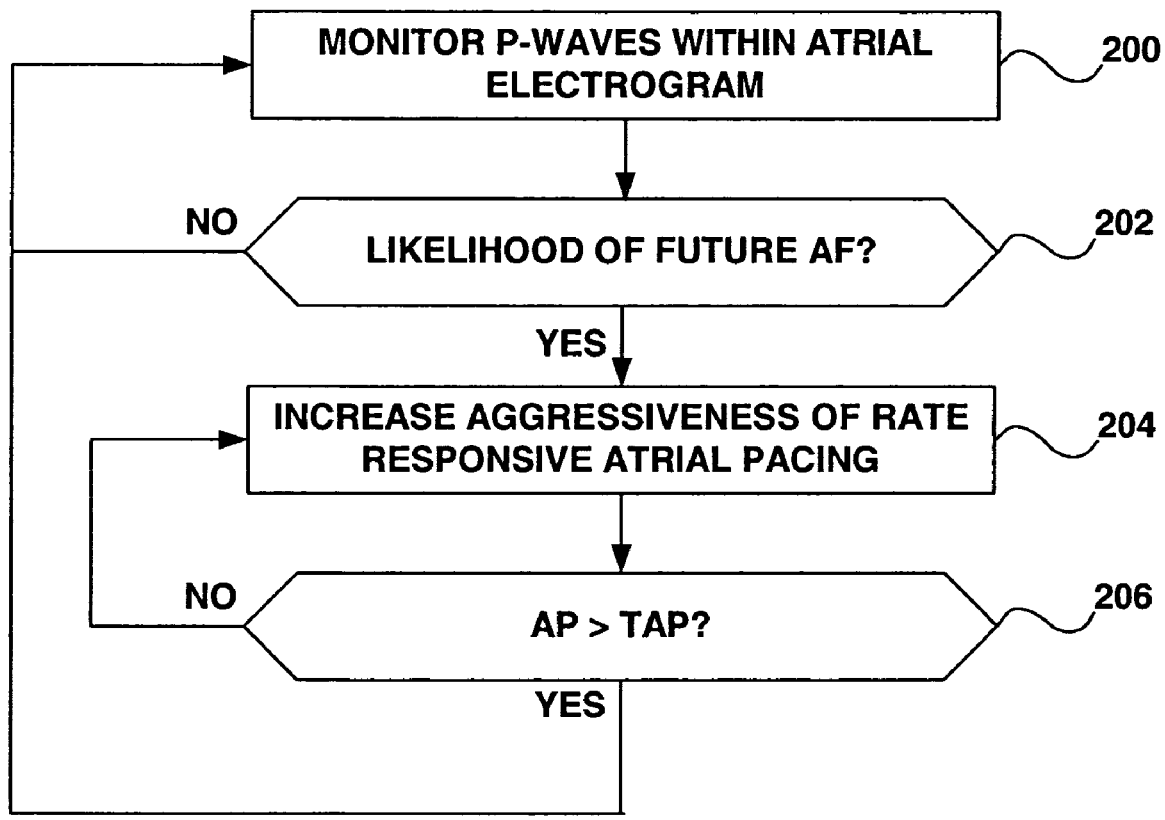
FIG. 11 is a flow diagram illustrating an exemplary mode of operation of the implantable medical device of FIG. 1 to modify a therapy based on detection of degradation of the atrial myocardium.

FIG. 11 is a flow diagram illustrating an exemplary mode of operation of IMD 10 to modify a therapy based on detection of degradation of the atrial myocardium. More particularly, FIG. 11 illustrates a mode of operation of IMD 10 to increase the aggressiveness of rate responsive atrial pacing in response to identification of a risk of atrial fibrillation posed by degradation of the atrial myocardium. Increased aggressiveness of rate responsive atrial pacing can prevent episodes of atrial fibrillation from occurring.

Microprocessor 50 monitors one or more characteristics of P-waves 92 within an atrial electrogram 90 (200), and identifies a likelihood of future atrial fibrillation resulting from degradation of the atrial myocardium (202) using any of the techniques described above. Microprocessor 50 increases the aggressiveness of rate responsive atrial pacing by, for example providing pacer timing/control circuitry 64 (FIG. 3) a new rate response function with a greater slope (204). For example, in exemplary embodiments microprocessor 50 adjusts sensor rate profiles, such as those embodied in the Kappa™ pacemakers commercially available from Medtronic, Inc.

Microprocessor 50 determines the percentage of atrial beats that are paced over a period of time, such as a minute, and compares this actual percentage (AP) to a target atrial pacing (TAP) percentage value is stored in a memory, such as RAM 72 (206). Microprocessor 50 receives indications of whether beats are paced or intrinsic from pacer timing/control circuitry 64. As shown in FIG. 11, microprocessor 50 increases the aggressiveness of rate responsive atrial pacing until the target is met.

Figure 12:
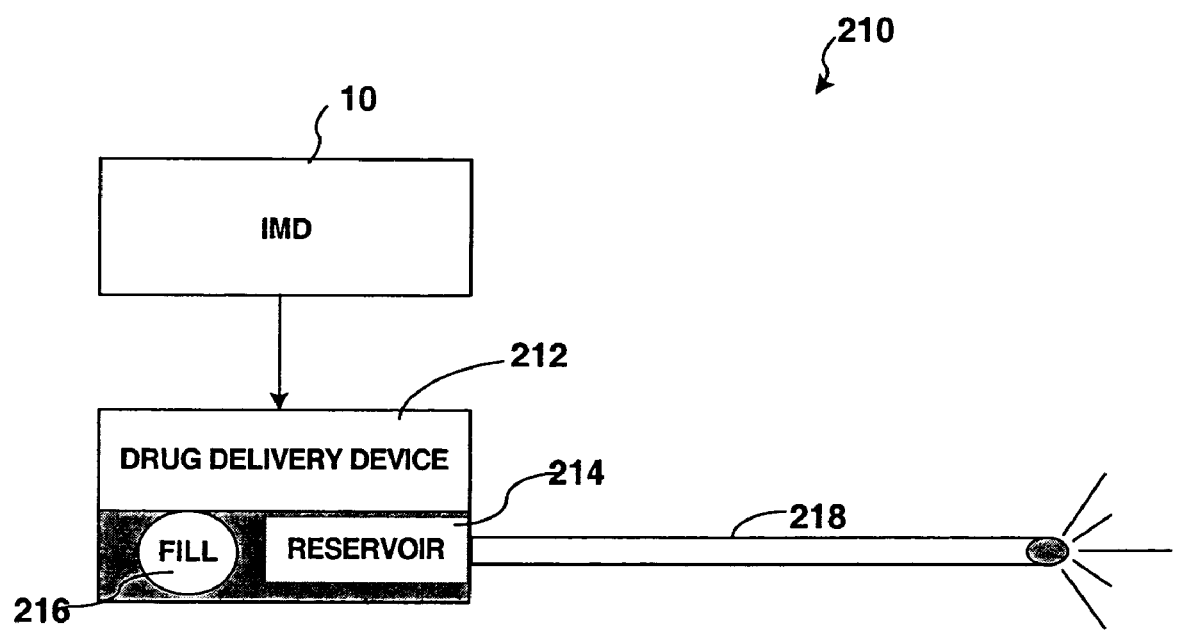
FIGS. 12 and 13 are block diagrams illustrating exemplary systems that include the implantable medical device of FIG. 1.
Figure 13:
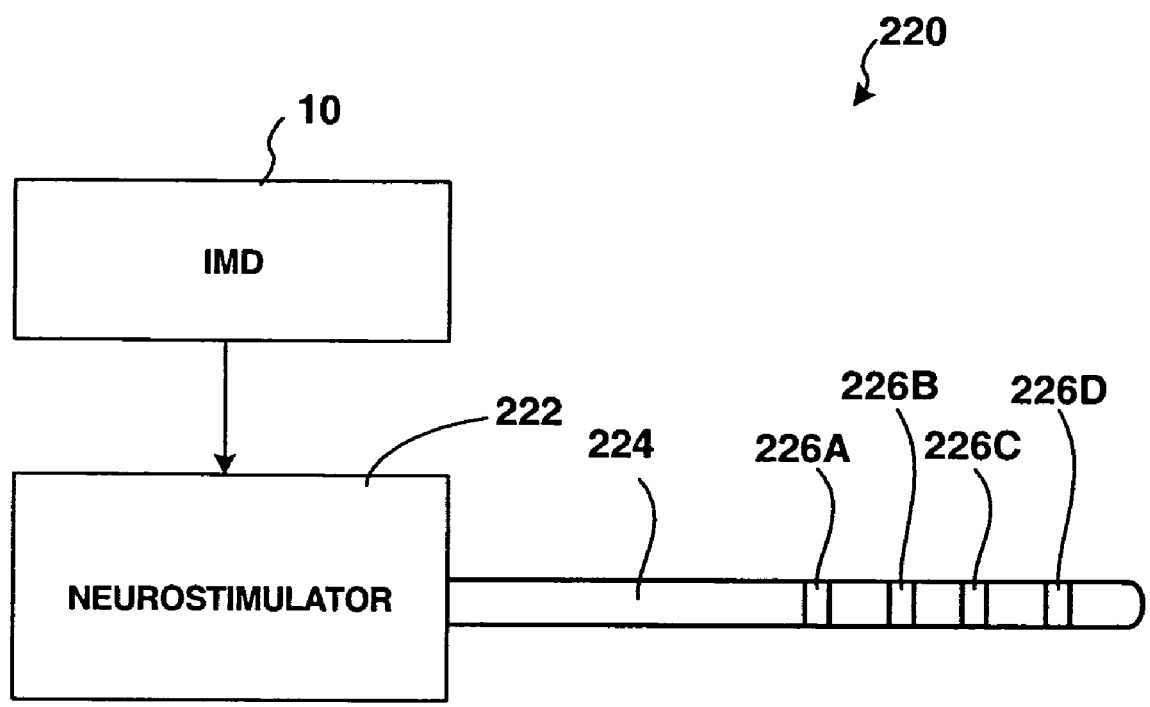

FIGS. 12 and 13 are block diagrams illustrating exemplary systems 210 and 220 that include IMD 10. System 210 illustrated in FIG. 12 includes a drug delivery device 212, which in exemplary embodiments is an implanted drug pump. Drug delivery device 212 includes a reservoir capable of holding at least one of a biological, genetic, or pharmacological agent to be delivered to patient 12, and a pump (not shown) for delivering the agent to a selected location via a catheter 218, or the like. Device 212 also includes a fill port 216 for refilling reservoir 214, which in exemplary embodiments takes the form of a resealable membrane that provides a syringe or the like with transcutaneous access to reservoir 214. An exemplary drug delivery device 212 is embodied in the Synchromed™ pumps commercially available from Medtronic, Inc.

IMD 10, and more specifically microprocessor 50, controls delivery of the agent or agents stored in reservoir 214 by delivery device 212. In some embodiments, microprocessor 50 directly controls a pump of device 12, while in other embodiments microprocessor 50 provides an indication to a processor of device 212 to cause the processor to initiate or modify delivery of the agent. In some embodiments, IMD 10 and device 212 form a single device within a common housing.

In exemplary embodiments, microprocessor 50 of IMD 10 controls delivery device 212 to initiate delivery of nitroglycerine or other drugs used to treat angina upon detection of impending angina, or thrombolytic drugs used to dissolve clots upon detection of ischemia or impending angina. In such embodiments, catheter 218 can positioned such that device 212 delivers the agents to heart 16.

System 220 depicted in FIG. 13 includes a neurostimulator 222 in addition to IMD 10. Neurostimulator 222 includes one or more leads 224 that carry one or more electrodes 226, and delivers neurostimulation to neural tissue of patient 12 via electrodes 226. In exemplary embodiments, neurostimulation is delivered in the form of electrical pulses. In the illustrated embodiment, lead 224 carries four electrodes 226A-D in a configuration suitable for delivery of neurostimulation to the spinal cord of patient 12. An exemplary neurostimulator 222 and lead combination is embodied in the Itrel™ neurostimulator and Pieces Quad™ leads commercially available from Medtronic, Inc.

IMD 10, and more specifically microprocessor 50, controls delivery of neurostimulation by neurostimulator 222. In some embodiments, microprocessor 50 directly controls generation of stimulation by neurostimulator 222, while in other embodiments microprocessor 50 provides an indication to a processor of neurostimulator 222 to cause the processor to initiate or modify delivery of neurostimulation. In some embodiments, IMD 10 and neurostimulator form a single device within a common housing.

In exemplary embodiments, microprocessor 50 of IMD 10 controls neurostimulator 222 to initiate delivery stimulation to the spinal cord of patient 12 in response to detection of impending angina. Spinal cord stimulation can increase blood flow to heat 16 and reduce the pain associated with angina. Additional detail regarding exemplary techniques for delivery of spinal cord stimulation in response to angina are discussed in commonly assigned U.S. Pat. No. 5,824,021, to Rise, which issued Oct. 20, 1998, and is incorporated herein by reference in its entirety.

Various embodiments of the invention have been described. However, one skilled in the art will recognize that various modifications can be made to these embodiments without departing from the scope of the claims. For example, although measurement of characteristics of P-waves has been described herein primarily as measurement of P-wave amplitudes, P-wave widths, and variability or dispersion or P-wave widths, the invention is not so limited. Measurement of characteristics can, for example, include measurement using template matching, such as that implemented in the Marquis™ implantable cardioverter-defibrillators commercially available from Medtronic, Inc., wavelet analysis, or Fourier analysis techniques to compare a current P-wave to previous P-waves or templates stored in memory.

As another example, instead of or in addition to increasing the aggressiveness of rate responsive pacing, some embodiments of the present invention increase the aggressiveness of atrial fibrillation prevention algorithms, such as those implemented in the AT500™ pacemaker commercially available from Medtronic, Inc. These and other embodiments are within the scope of the following claims.

The invention claimed is:

1. A method of monitoring electrical activity of a heart, comprising:

receiving a signal that represents electrical activity within the heart of a patient via electrodes;

processing the signal to monitor dispersions of widths of P-waves;

determining whether increases in the monitored dispersions are one of long term increases and short term increases; and distinguishing between medically significant changes in the heart based upon the determining whether increases in the monitored dispersions are one of long term increases and short term increases and providing an indication thereof.

2. The method of claim 1, wherein processing the signal to monitor dispersions comprises:

determining first dispersions for a first subset of P-waves and second dispersions for a second subset of the P-waves; and comparing the first and second dispersions.

3. The method of claim 1, wherein processing the signal to monitor dispersions comprises:

measuring one of differences between current and previous dispersions and a ratio of current and previous dispersions; and comparing the measured one of differences between current and previous dispersions and a ratio of current and previous dispersions to a template stored in a memory.

4. The method of claim 1, wherein distinguishing between medically significant changes comprises detecting degradation of an atrial myocardium in response to the increases being determined to be long term, and identifying impending angina in response to the increases being determined to be short term.

5. The method of claim 4, further comprising confirming the detecting of impending angina, wherein the confirming comprises determining one of whether shortening of QT intervals has occurred and whether an activity level has increased.

6. The method of claim 1, further comprising:

storing the indication of the medically significant change in the heart within a memory; and providing the indication of the medically significant change in the heart to a user via a programming device upon interrogation by the programming device.

7. The method of claim 1, further comprising activating an alarm based on the indication of the medically significant change in the heart.

8. The method of claim 1, further comprising controlling delivery of therapy to the patient based on the indication of the medically significant change in the heart.

9. The method of claim 8, wherein controlling delivery of therapy comprises one of switching from an atrial-tracking pacing mode to a VVI pacing mode based on the dispersions, decreasing a maximum tracking rate for an atrial-tracking pacing mode based on the indication of the medically significant change in the heart, increasing aggressiveness of rate responsive atrial pacing based on the indication of the medically significant change in the heart, controlling delivery of a drug by a drug delivery device based on the indication of the medically significant change in the heart and controlling delivery of neurostimulation based on the indication of the medically significant change in the heart.

10. The method of claim 1, wherein processing the signal to monitor dispersions of widths of P-waves comprises:

calculating a dispersion for a current period of time having a predetermined length; and comparing the dispersion calculated for the current period of time to a dispersion calculated a predetermined time prior to the current period of time, wherein the predetermined length of the current period of time and the predetermined time prior to the current period of time vary in response to the indication of the medically significant change in the heart.

11. An implantable medical device comprising:

electrodes to detect a signal that represents electrical activity within a heart of a patient; and a processor to monitor dispersions of widths of P-waves, determine whether increases in the monitored dispersions are one of long term increases and short term increases, and distinguish between medically significant changes in the heart based upon the determination whether increases in the monitored dispersions are one of long term increases and short term increases and provide an indication thereof.

12. The device of claim 11, wherein the processor determines first dispersions for a first subset of P-waves and second dispersions for a second subset of the P-waves, and compares the first and second dispersions.

13. The device of claim 11, wherein the processor measures one of differences between current and previous dispersions and a ratio of current and previous dispersions and compares the measured one of differences between current and previous dispersions and a ratio of current and previous dispersions to a template stored in a memory.

14. The device of claim 11, wherein the processor detects degradation of an atrial myocardium in response to the increases being determined to be long term and detects impending angina in response to the increases being determined to be short term.

15. The device of claim 14, wherein the processor determines, in response to impending angina being identified, one of whether shortening of QT intervals has occurred and whether an activity level has increased to confirm the identifying of impending angina.

16. The device of claim 11, further comprising:

a memory; and a telemetry circuit, wherein the processor stores the indication of the medically significant change in the heart within the memory, and provides the indication of the medically significant change in the heart to a user via the telemetry circuit and a programming device upon interrogation by the programming device.

17. The device of claim 11, further comprising an alarm, wherein the processor activates the alarm based on the distinguishing.

18. The device of claim 11, wherein the processor performs one of controlling delivery of pacing pulses to a ventricle of the heart and switching from an atrial-tracking pacing mode to a VVI pacing mode based on the indication of the medically significant change in the heart, controlling delivery of pacing pulses to a ventricle of the heart and decreasing a maximum tracking rate for an atrial-tracking pacing mode based on the indication of the medically significant change in the heart, controlling delivery of pacing pulses to an atrium of the heart and increasing aggressiveness of rate responsive atrial pacing based on the indication of the medically significant chance in the heart, controlling delivery of a drug by a drug delivery device based on the indication of the medically significant change in the heart, and controlling delivery of neurostimulation based on the indication of the medically significant change in the heart.

19. The device of claim 11, wherein the monitoring of dispersions of widths of P-waves by the processor comprises:

calculating a dispersion for a current period of time having a predetermined length; and comparing the dispersion calculated for the current period of time to a dispersion calculated a predetermined time prior to the current period of time, wherein the predetermined length of the current period of time and the predetermined time prior to the current period of time vary in response to the indication of the medically significant chance in the heart.

20. A computer-readable medium having computer-executable instructions for performing a method, comprising:
monitoring dispersions of widths of P-waves within a signal that represents electrical activity within a heart of a patient; determining whether increases in the monitored dispersions are one of long term increases and short term increases; and
distinguishing between medically significant changes in the heart based upon the determining whether increases in the monitored dispersions are one of long term increases and short term increases and providing an indication thereof.

21. The computer-readable medium of claim 20, wherein the monitoring comprises:
determining first dispersions for a first subset of P-waves and second dispersions for a second subset of the P-waves; and
comparing the first and second dispersions.

22. The computer-readable medium of claim 20, wherein the monitoring comprises:
measuring one of differences between current and previous dispersions and a ratio of current and previous dispersions; and
comparing the measured one of differences between current and previous dispersions and a ratio of current and previous dispersions to a template stored in a memory.

23. The computer-readable medium of claim 20, wherein distinguishing between medically significant changes comprises detecting degradation of an atrial myocardium in response to the increases being determined to be long term, and detecting an increased probability of an occurrence of angina in response to the increases being determined to be short term.

24. The computer readable medium of claim 23, further comprising confirming the detecting of an increased probability of an occurrence of angina, wherein the confirming comprises determining one of whether shortening of QT intervals has occurred and whether an activity level has increased.

25. The computer-readable medium of claim 20, further comprising controlling delivery of therapy to the patient based on the indication of the medically significant change in the heart.

26. The computer-readable medium of claim 25, wherein controlling delivery of therapy includes one of switching from an atrial-tracking pacing mode to a VVI pacing mode based on the indication of the medically significant change in the heart, decreasing a maximum tracking rate for atrial-tracking pacing mode based on the indication of the medically significant change in the heart, increasing aggressiveness of rate responsive atrial pacing based on the indication of the medically significant change in the heart, controlling delivery of a drug by a drug delivery device based on the indication of the medically significant change in the heart, and controlling delivery of neurostimulation based on the indication of the medically significant change in the heart.

27. The computer readable medium of claim 20, wherein monitoring dispersions of widths of P-waves comprises:
calculating a dispersion for a current period of time having a predetermined length; and
comparing the dispersion calculated for the current period of time to a dispersion calculated a predetermined time prior to the current period of time, wherein the predetermined length of the current period of time and the predetermined time prior to the current period of time vary in response to the indication of the medically significant change in the heart.

28. An implantable medical device system comprising:
a therapy delivery device to deliver a therapy to a patient; and
a monitoring device to monitor dispersions of widths of P-waves, determine whether increases in the monitored dispersions are one of long term increases and short term increases, and distinguish between medically significant changes in the heart based upon the determination whether increases in the monitored dispersions are one of long term increases and short term increases and provide an indication thereof, and control delivery of therapy by the therapy delivery device based on the indication of the medically significant change in the heart by the monitoring device.

29. The system of claim 28, wherein the therapy delivery device is a drug delivery device, and the monitoring device controls delivery of a drug by the drug delivery device based on the indication of the medically significant change in the heart.

30. The system of claim 29, wherein the therapy delivery device is a neurostimulator, and the monitoring device controls delivery of neurostimulation by the neurostimulator based on the indication of the medically significant change in the heart.

31. The system of claim 28, wherein the monitoring of dispersions of widths of P-waves by the monitoring device comprises:
calculating a dispersion for a current period of time having a predetermined length; and
comparing the dispersion calculated for the current period of time to a dispersion calculated a predetermined time prior to the current period of time, wherein the predetermined length of the current period of time and the predetermined time prior to the current period of time vary in response to the indication of the medically significant change in the heart.

32. The system of claim 28, wherein the monitoring device detects degradation of an atrial myocardium in response to the increases being determined to be long term, detects impending angina in response to the increases being determined to be short term, and confirms the detecting of impending angina, wherein the confirming comprises determining one of whether shortening of QT intervals has occurred and whether an activity level has increased.

* * * * *

UNITED STATES PATENT AND TRADEMARK OFFICE
CERTIFICATE OF CORRECTION

PATENT NO.        : 7,620,446 B2
APPLICATION NO.   : 10/631614
DATED             : November 17, 2009
INVENTOR(S)       : Bozidar Ferek-Petric It is certified that error appears in the above-identified patent and that said Letters Patent is hereby corrected as shown below:

Column 14
Line 58, delete "chance" and insert -- change -- therefor;

Signed and Sealed this

Fourth Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,620,446 B2  Page 1 of 1
APPLICATION NO. : 10/631614
DATED : November 17, 2009
INVENTOR(S) : Bozidar Ferek-Petric It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1079 days.

Signed and Sealed this

Twenty-sixth Day of October, 2010

David J. Kappos
*Director of the United States Patent and Trademark Office*